United States Patent [19]
Magovern

[11] Patent Number: 5,979,456
[45] Date of Patent: *Nov. 9, 1999

[54] APPARATUS AND METHOD FOR REVERSIBLY RESHAPING A BODY PART

[76] Inventor: George J. Magovern, 251 Old Mill Rd., Pittsburgh, Pa. 15238

[*] Notice: This patent issued on a continued prosecution application filed under 37 CFR 1.53(d), and is subject to the twenty year patent term provisions of 35 U.S.C. 154(a)(2).

[21] Appl. No.: 08/636,135

[22] Filed: Apr. 22, 1996

[51] Int. Cl.$^6$ .................................................... A61B 19/00
[52] U.S. Cl. ............................................................ 128/899
[58] Field of Search ........................... 128/899, 716–719; 602/6–8; 623/1, 11, 16; 600/3, 30, 31, 37, 529–531; 607/42–48

[56] References Cited

U.S. PATENT DOCUMENTS

| | | | |
|---|---|---|---|
| 3,868,956 | 3/1975 | Alfidi et al. | 606/194 |
| 4,685,453 | 8/1987 | Guignard et al. | 602/7 |
| 4,969,890 | 11/1990 | Sugita et al. | 606/192 |
| 5,147,370 | 9/1992 | McNamara et al. | 623/1 X |
| 5,197,978 | 3/1993 | Hess | 623/1 |
| 5,409,017 | 4/1995 | Lowe . | |
| 5,433,193 | 7/1995 | Sanders et al. . | |
| 5,502,067 | 3/1996 | Morgan . | |
| 5,545,210 | 8/1996 | Hess et al. | 623/1 |
| 5,562,641 | 10/1996 | Flomenblit et al. | 623/1 |

*Primary Examiner*—Samuerl Gilbert
*Attorney, Agent, or Firm*—Duane, Morris & Heckscher LLP

[57] ABSTRACT

An apparatus and method for reversibly modifying the shape of a selected portion of the body such as the pharynx, to produce a desired result, for example, to overcome obstructive sleep apnea by urging open the pharynx. The apparatus includes a preconfigured structure having a shape-memory with an activated shape and a quiescent shape. The preconfigured structure is shaped to conform to the selected portion of the body. The shape-memory is responsive to activation energy and urges the preconfigured structure from the quiescent shape to the activated shape. Furthermore, the activated shape of the preconfigured structure exerts a force on the selected portion, thereby modifying the shape of the selected portion. The preconfigured structure can be attached to an exterior surface of, or can be implanted within the body proximate to, the selected portion of the body. The apparatus can include an energy source coupled to the preconfigured structure for providing the activation energy, responsive to a predetermined stimulus and can be attached external to, or implanted within, the body. The invention also provides a method for reversibly modifying the shape of a selected portion of a body. The method includes attaching a preconfigured shape-memory structure to the selected portion of the body; and applying the activation energy to the preconfigured structure with an energy source, thereby the preconfigured shape-memory structure from the quiescent shape to the activated shape.

56 Claims, 11 Drawing Sheets

APPARATUS AND METHOD FOR REVERSIBLY RESHAPING A BODY PART

FIELD OF THE INVENTION

The invention relates to prosthetic devices, in particular, the invention is directed to reversibly reshaping a body part for the purpose of treating a disease.

BACKGROUND OF THE ART

Sleep apnea is a syndrome in which the structure of the airway changes during sleep, resulting in periods of apnea. Although the initial symptoms are related to the apnea and loss of sleep, the prolonged periods of hypoxia due to the apnea eventually result in profound physiologic changes. One commonly-diagnosed sleep apnea syndrome is obstructive sleep apnea (OSA). OSA may be defined as the absence of air flow combined with persistent respiratory effort during sleep. While the upper airway normally remains patent during quiet breathing and wakefulness in sleep, patients with OSA can have repetitive periods of upper airway closure during sleep. The upper airway closures usually occur at various sites in the pharynx.

Areas responsible for inducing OSA, seen in FIG. 1, are considered to be the nose 1, the nasopharynx 2, the soft palate 3, the uvula 4, the palatal tonsils 5, the lateral and posterior walls of the pharynx 6 and 7, respectively, and base of the tongue 8. Stenosis of the airway in each area alone, or in combination, can result in apnea during sleep. However, other areas also may be involved in producing OSA. The patency of the potentially-collapsible pharynx 9 during inspiration depends on the balance between subatmospheric pressure in the pharyngeal airway 9 and airway-dilating forces generated by the pharyngeal muscles 6,7. The pressure required to collapse the upper airway in the absence of upper airway muscle activity is normally subatmospheric.

OSA is not a benign disease. It has been estimated that, in one year, 58,000 motor vehicle accidents involved a sleep apnea patient. These patients also have a higher incidence of stroke, right heart failure, and an increased mortality rate when there are greater than 20 apneic episodes per hour of sleep. Sleep apnea patients tend to have irresistible "sleep attacks" and higher incidence of anxiety, depression, and sexual dysfunction.

In general, the principle of OSA treatment is to remove the upper airway obstruction, most likely a pharyngeal occlusion. Although the treatment regimen must be tailored to the individual, his symptoms, sleep study results, and physical findings, therapeutic options tend to fall into four broad categories. First, aggravating factors such as alcohol or sedatives are identified and eliminated, and the patient undergoes sustained weight reduction.

Second, pharmacologically-active substances such as protriptyline and pilocarpine may be used. One example of a method for treating sleep apnea using pharmacologically-active agents may be found in U.S. Pat. No. 5,407,953 to Morgan in which sleep apnea is treated by administering a compound that results; in the release of pilocarpine to the nasopharynx and hypopharynx in an amount effective to improve the tone of the pharyngeal musculature, thus reducing or eliminating sleep apnea. However, the administration of certain pharmacologically-active substances may be contraindicated in some patients, or may cause unexpected side effects.

Third, surgical intervention such as transtracheal oxygen therapy (TTO), uvulopalatopharyngoplasty (UPPP), tracheotomy, and even suction-assisted lipectomy, may be employed.

Fourth, mechanical and prosthetic devices including continuous positive airway pressure (CPAP), bi-level positive airway pressure (BiPAP), and dental appliances that advance the mandible forward during sleep or that reposition the tongue, can be used. One example of a mandible-repositioning dental appliance is found in U.S. Pat. No. 5,409,017 to Lowe. This appliance forces the lower mandible outward and attempts to maintain airway patency.

One of the most effective treatments for OSA involves the use of a mechanical device such as CPAP or BiPAP. When used appropriately, positive airway pressure methods tend to raise the pharyngeal pressure above the closing pressure, thereby overcoming the pharyngeal obstruction. Because CPAP and BiPAP devices may produce nasal stuffiness and feelings of claustrophobia, patient compliance often is a problem. Indeed, some estimates place actual patient compliance with CPAP and BiPAP devices at less than 50 percent. Although it is still unknown how much CPAP or BiPAP use is sufficient to prevent daytime hypersomnolence, sleeping without positive airway pressure for one night can reverse the beneficial effects of one month of positive airway pressure use.

One example of a positive airway pressure breathing gas delivery method and apparatus is found in U.S. Pat. No. 5,433,193 to Sanders, et al. This device treats sleep apnea through the application of alternating high and low level positive airway pressure within the airway of the patient, with the high and low airway pressure being coordinated with a spontaneous respiration of the patient.

Many treatment modalities are ineffective for certain patients. Furthermore, the many effective methods often are sufficiently obtrusive as to adversely impact patient compliance and, therefore, the actual effectiveness of the treatment. What is needed, then, is an apparatus and method for reversibly modifying the shape of a selected portion of the body such as, for example, the pharynx, to produce a desired result, for example, to overcome obstructive sleep apnea by urging open the pharynx.

SUMMARY OF THE INVENTION

The invention provides an apparatus and method for reversibly modifying the shape of a selected portion of the body such as, for example, the pharynx, to produce a desired result, for example, to overcome obstructive sleep apnea by urging open the pharynx. The apparatus includes a preconfigured structure having a shape-memory with an activated shape and a quiescent shape. The preconfigured structure is shaped to conform to, and is connectable to, the selected portion of the body. The shape-memory is responsive to an activation energy and urges the preconfigured structure from the quiescent shape to the activated shape. Furthermore, the activated shape of the preconfigured structure exerts a force on the selected portion, thereby tending to modify the shape of the selected portion. In contradistinction, the shape-memory responds to removal of the activation energy by urging the preconfigured structure from the activated shape to the quiescent shape and at least partially removing the force on the selected portion, thus tending to restore the shape of the selected portion.

The preconfigured structure can be attached to an exterior surface of, or can be implanted within the body proximate to, the selected portion of the body.

The apparatus can include an energy source coupled to the preconfigured structure for providing the activation energy, responsive to a predetermined stimulus. The energy source can be an electrical, a mechanical, a thermal, an electromagnetic energy source, or a combination thereof. The energy source can be attached external to, or implanted within, the body. In addition, the predetermined stimulus can be a mechanical, an electrical, an electromagnetic, an acoustic, an optical stimulus, or a combination thereof.

It is preferred that exerting the force on the body part is performed gradatim so that modifying the shape of the selected portion is substantially unobtrusive. It is also preferred that the activation energy is intermittently applied to accommodate a function of the body.

The preconfigured structure of the apparatus can be a first linear form, a first planar form, or a combination thereof. The first planar form can include multiple second linear forms and second planar forms, with each of the forms being selectively activatable.

In certain embodiments of the apparatus, it is preferred that the selected portion of the body is a pharyngeal wall and the activated shape of the structure exerts outward force on the wall, thereby tending to urge open the pharynx. The preconfigured structure can be attached to an exterior surface of the neck proximate to, and connected with, the pharyngeal wall. In the alternative the preconfigured structure can be implanted within a tissue proximate to the pharyngeal wall, including the superior, middle, and inferior constrictor muscles which form a portion of the pharyngeal wall.

For external implementations, the apparatus also can include an adhesive form at least partially interposed between the preconfigured structure and the exterior surface of the neck, removably attaching the preconfigured structure to the exterior surface of the neck. The apparatus further can include a collar and at least one adhesive pad. The collar can have the preconfigured structure therein; and the adhesive pad removably attaching the preconfigured structure to the exterior surface of the neck.

The preconfigured structure can be one of a linear form, a planar form, or a composite form, with the preconfigured structure being affixed to the tissues proximate to, or constituting, the pharyngeal wall. The linear form can be one of a single-stranded thread, a multi-stranded braid, or a strip; the planar form can be a mesh or a plate; and the composite form can include a plurality of the linear form, the planar form, or both.

It is preferred that the activation energy be applied intermittently, gradatim, or both so that the modifying and restoring of the selected body part is substantially unobtrusive, accommodating a body function.

The selected portion of the body can also be the chest or the abdomen, and the activated shape of the structure can exert a force upon that selected portion, thereby tending to assist respiratory function.

The invention also provides a method for reversibly modifying the shape of a selected portion of a body. The method includes attaching a preconfigured shape-memory structure to the selected portion of the body; and applying the activation energy to the preconfigured structure with an energy source, thereby the preconfigured shape-memory structure from the quiescent shape to the activated shape. The structure has a shape-memory being shaped to generally conform to the selected portion of the body and be responsive to an activation energy. The structure has an activated shape and a quiescent shape. The activated shape exerts a force, thereby tending to modify the shape of the selected portion. The step of applying the activation energy includes sensing a predetermined condition; generating a stimulus responsive to the predetermined condition; and generating the activation energy responsive to the stimulus.

The step of attaching the structure to the body portion includes interposing the adhesive pad between the selected portion and the preconfigured shape-memory structure. In this embodiment, the structure is at least partially embedded in the adhesive pad, and the adhesive pad is removably attached to an exterior surface of the body proximate to the selected portion. As a result, the adhesive pad transmits the force to the external surface from the activated shape, responsive to the activation energy. The step of attaching also can include removably attaching a collar, belt, or band to the selected portion, the collar, belt, and band having the preconfigured shape-memory structure therein. The method also comprehends attaching the structure to the body portion implanting the preconfigured shape-memory structure in the body proximate to the selected portion. The method can also include selectively generating the activation energy responsive to the stimulus, either intermittently, gradatim, or both so that the reversibly modifying is substantially unobtrusive.

DESCRIPTION OF THE EMBODIMENTS

Figure 1:
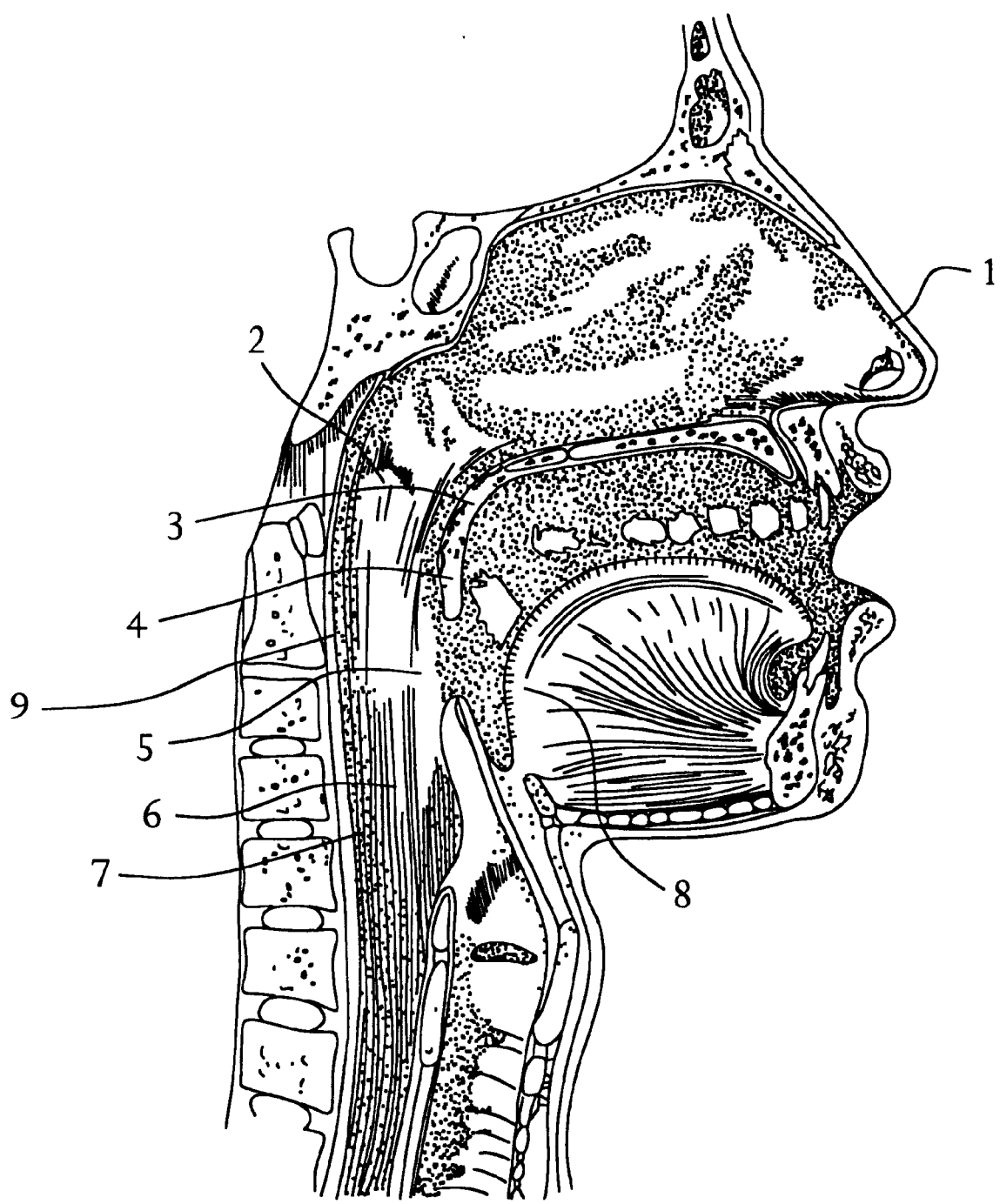
FIG. 1 illustrates a sectional view of a human head and neck showing anatomical structures associated with obstructive sleep apnea.

The invention herein provides an apparatus and method for modifying the shape of a selected portion of the body. The apparatus includes a preconfigured structure that has a shapememory. The structure generally is shaped to conform to a selected portion of the body. The preconfigured structure assumes an activated shape responsive to an activation energy, thus modifying the selected body portion. The quiescent shape of the structure, and the body portion attached thereto, results from the removal of the activation energy. The activation energy can be applied gradatim so that the modifying and restoration of the selected body portion is substantially unobtrusive to the patient. Furthermore, the activation energy can be intermittently applied, to accommodate a function of the body, for example, the reflexive upper pharyngeal functions of swallowing and coughing.

The apparatus can be attached to an exterior surface of the selected body portion, or may be implanted within the body. Furthermore, an energy source can be coupled with the preconfigured structure to supply the activation energy thereto, responsive to a predetermined stimulus. The energy source can be an electrical, mechanical, thermal, or electromagnetic energy source, which may be located external to, or implanted within, the body. A predetermined stimulus can be mechanical, acoustic, optical, electrical, or electromagnetic stimulus and, indeed, can include stimuli such as, for example, brain wave or heart signals, blood gas analyzer signals, or patient-generated sounds such as snoring or gasping for air. The predetermined stimulus can reversibly reshape the desired body part by urging the preconfigured structure into the activated state and the quiescent shape. The apparatus can be configured such that at least a portion of the activation energy is applied to the musculature surrounding the implanted preconfigured structure thereby causing tissue stimulation or muscle contraction and, thus, augmenting the action of the preconfigured structure.

The intermittent application of activation energy can be generally synchronized in time and amplitude with body functions so that the natural movement of the selected body portion can be mirrored by the preconfigured structure, further contributing to the unobtrusiveness of the apparatus. It is preferred that, in most embodiments of the invention herein, the application and removal of activation energy and the resulting movement of the preconfigured structure do not produce arousal in a sleeping patient.

The structure can be generally of a linear form, a planar form, or a composite form. A linear form can take the configuration of at least one single-stranded thread, a multi-stranded braid, a strap, or a "finger, " of shape-memory material. A planar form can include a wire mesh, a thin plate of shape-memory material, and the like. A composite-form structure can include both linear and planar forms of shape-memory material which provides flexibility in tailoring the shape and functionality of the device to the individual patient, as functionally indicated.

Although many shape-memory materials may be used, a nickel-titanium alloy (NiTi) is suitable. One such NiTi alloy is manufactured, for example, by Shape Memory Applications, Inc., Santa Clara, Calif. In general, metallic shape-memory alloys, such as NiTi, CuZnAl, and CuAlNi alloys, undergo a transformation in their crystal structure when cooled from the high-temperature austenite form, which is generally stronger, to the low-temperature martensite form, which is weaker. When a shape-memory material is in its martensitic form, it is easily deformed to a new shape. However, when the material is heated through its transformation temperature, it reverts to austenite and recovers its previous shape with great force. The temperature at which the material reverses its high temperature form when heated can be adjusted by slight changes in material composition and through heat treatment. The shape-memory process can be made to occur over a range of a few degrees, if necessary, and the shape transition can be made to occur millions of times. Heating may be effected, for example, by passing an electric current through the material.

Some shape-memory materials can be made to exhibit shape-memory only upon heating (one-way shape-memory), or also can undergo a shape change upon cooling (two-way shape memory). Shape-memory materials are available in many forms including, for example, wires, rods, ribbons, strips, sheets, and microtubing, and can be used to fabricate shape-memory structures having linear, planar and composite forms.

Figure 2:
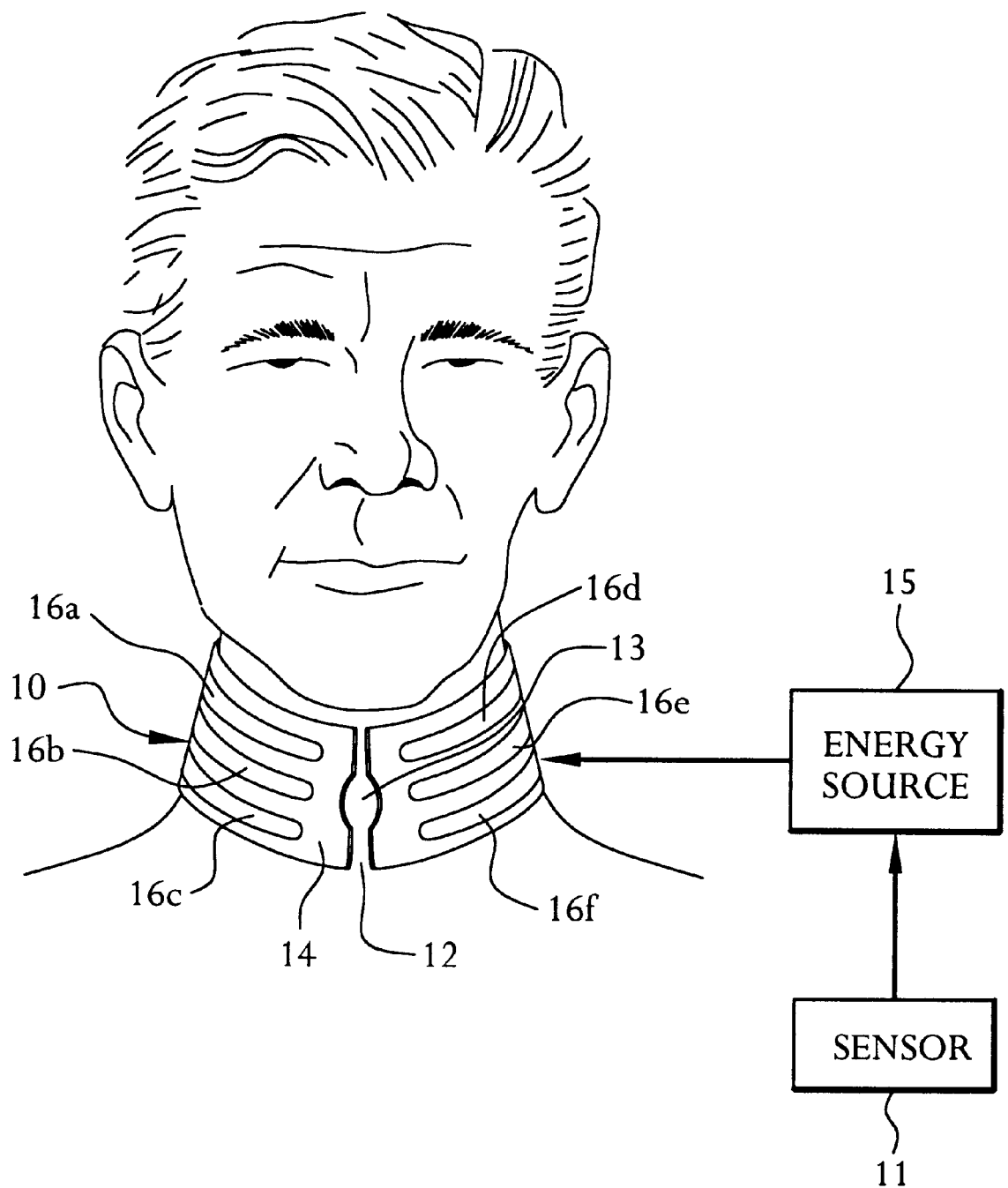
FIG. 2 is an illustration of an embodiment of a linear form the apparatus according to the invention herein adapted to be externally-disposed on a patient, using an adhesive sheet.

FIG. 2 illustrates an embodiment of an externally-applied apparatus which can be used to treat a condition, for example, OSA, by reversibly reshaping a selected body portion. The shape-memory structure 10 can be attached, usually removably, to the neck 12 proximate to the pharynx 13, using an adhesive sheet 14, or pad. In such an embodiment, the preconfigured shape-memory structure 10 can be at least partially embedded in adhesive sheet 14, so that an afflicted patient can apply the apparatus to the surface of neck 12, for example, at bedtime. The patient then can connect preconfigured shape-memory structure 10 to an energy source 15, which activates structure 10 responsive to a predetermined stimulus, as sensed by sensor 11. By assuming the activated shape, structure 10 in this embodiment applies an outward force to the cervical tissues and muscles. The walls of the pharynx are urged outward, thereby opening the upper airway. By controlling the application and removal of the activation energy gradatim, i.e. in a measured or graduated way, the forces exerted on the tissues and muscles are gradual and gentle enough to not arouse a sleeping patient, and remain substantially unobtrusive to the device wearer.

In the case of an externally-applied preconfigured shape-memory structure, it may be desirable for the energy source to be heat from the patient's body. When structure 10 is applied to the patient's neck 12, the patient's body heat can provide the activation energy needed to urge structure 10 into its activated shape, thereby urging the pharyngeal wall outward. Other energy source, 15 also may be used, including an electrical energy source such as a battery, a mechanical energy source including, for example, ultrasonic acoustic wave devices, or an electromagnetic energy source, such as magnetic induction device.

Figure 3:
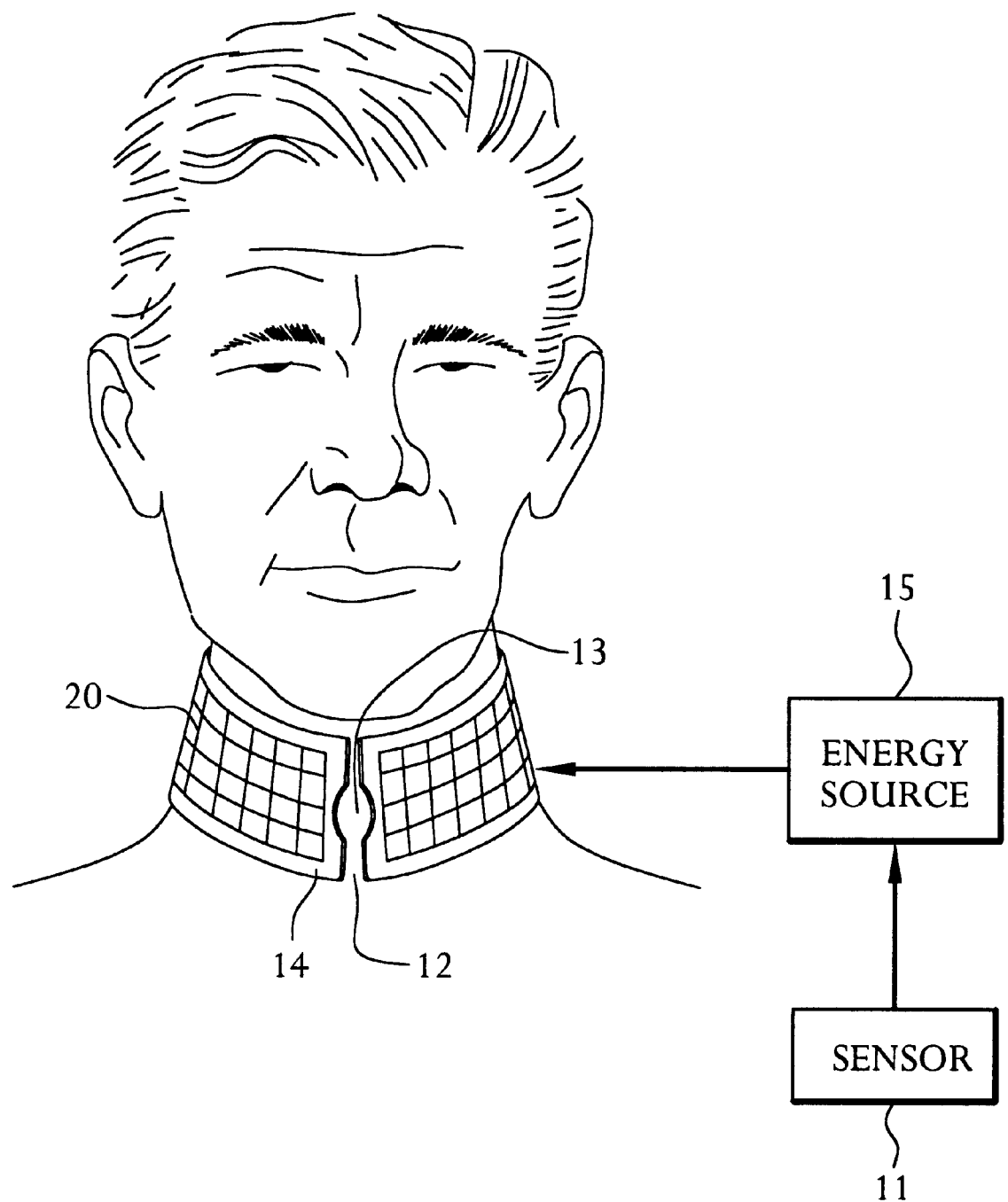
FIG. 3 is an illustration of an embodiment of a planar form of the apparatus according to the invention herein adapted to be externally-disposed on a patient, using an adhesive sheet.

Although FIG. 2 illustrates a linear form of structure 10 in which laterally-placed bands 16a–f are used, FIG. 3 illustrates that a planar form, for example, mesh 20, can be embedded in adhesive sheet 14. Similar to structure 10 in FIG. 2, mesh 20, can be activated by energy source 15, in response to a predetermined stimulus that is detected by sensor 11.

Figure 4:
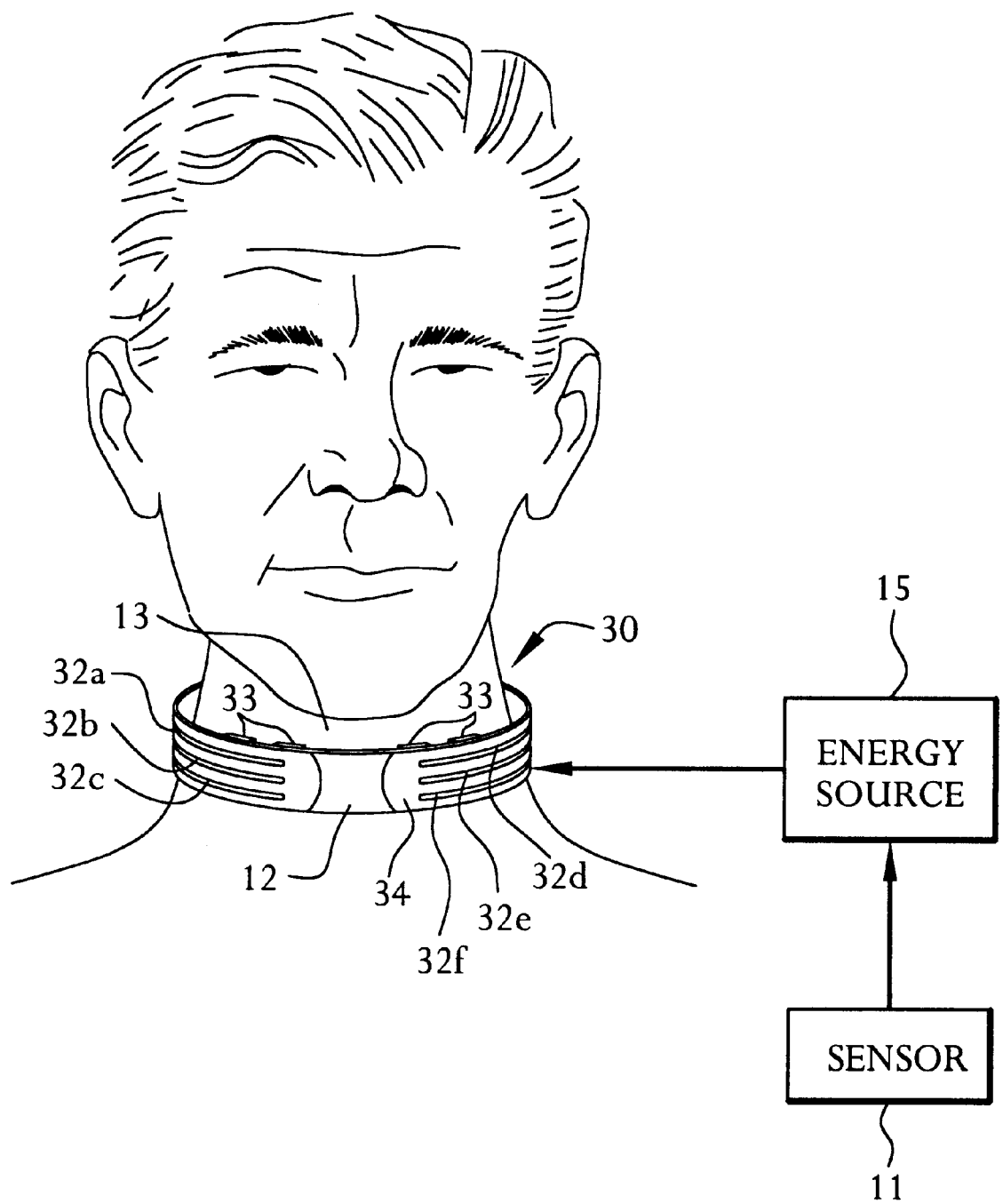
FIG. 4 is an illustration of an embodiment of a linear form of the apparatus according to the invention herein adapted to be externally-disposed on a patient, using a collar.

Another embodiment of an externally-applied preconfigured shape-memory structure 30, seen in FIG. 4, can employ a linear form 32a–f that is embedded in a removable collar 34. In this embodiment, structure 30 can be attached to the patient's neck 12 proximate to the pharynx 13 using a disposable adhesive sheet or pads 33 which, in turn, can be removably attached to the structure-containing collar 34. In this embodiment, mechanical, electrical, thermal, and electromagnetic energy source, 15 also may be used to activate structure 30, in conjunction with sensor 11, preferably in an unobtrusive manner that does not arouse the wearer from sleep.

Figure 5:
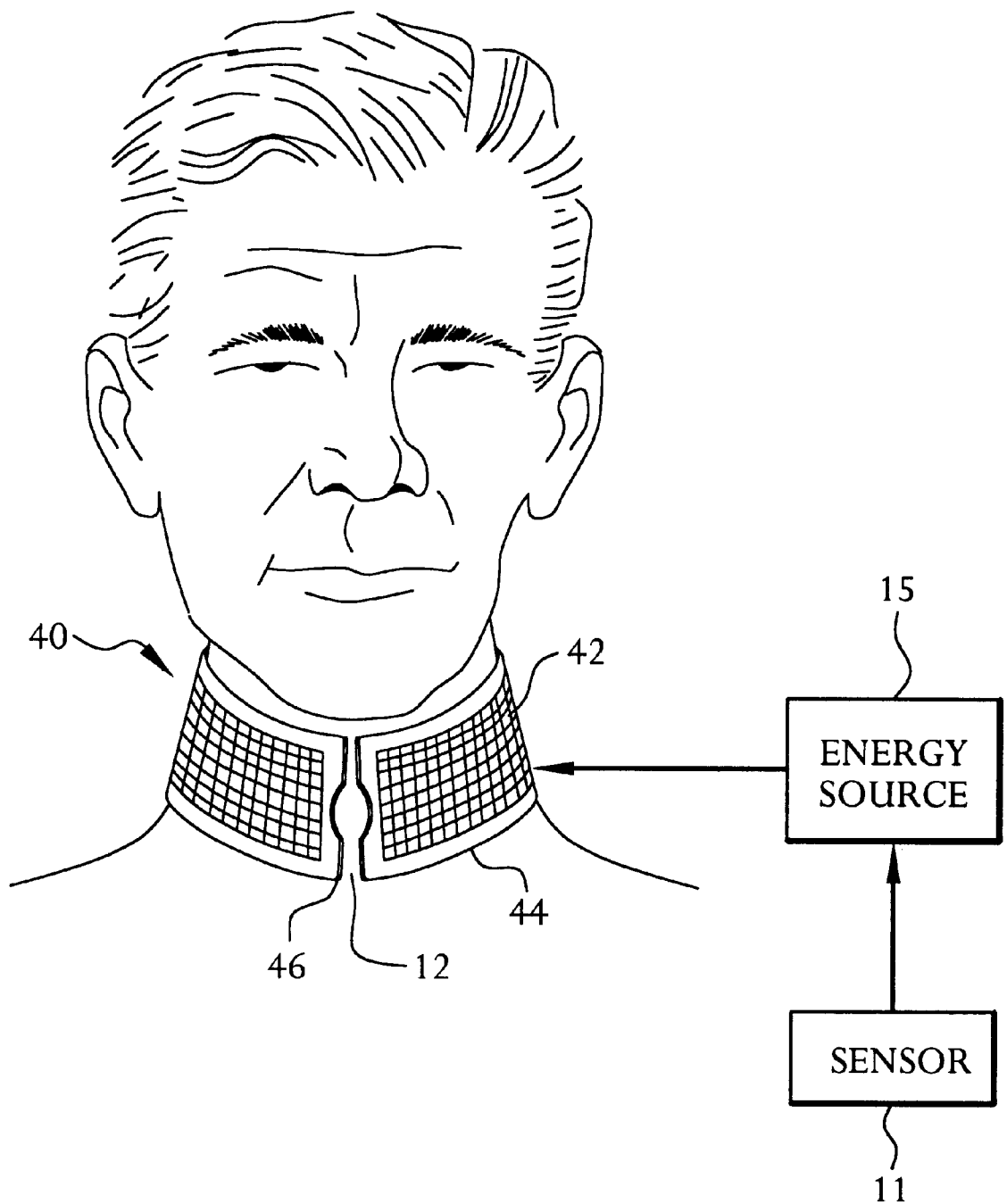
FIG. 5 is an illustration of an embodiment of a planar form of the apparatus according to the invention herein adapted to be externally-disposed on a patient, using a collar.

In still another embodiment of the invention herein, as seen in FIG. 5, externally-applied preconfigured shape-memory structure 40 can be a planar form, such as mesh 42, which is embedded in collar 44. Similar to collar 34 in FIG. 4, collar 44 can be attached to neck 12 by one or more adhesive pads, or by adhesive sheet 46, which collar 44 and sheet 46 can be releasably connected together using, for example, hook and loop fabric strips (not shown).

Figure 6:
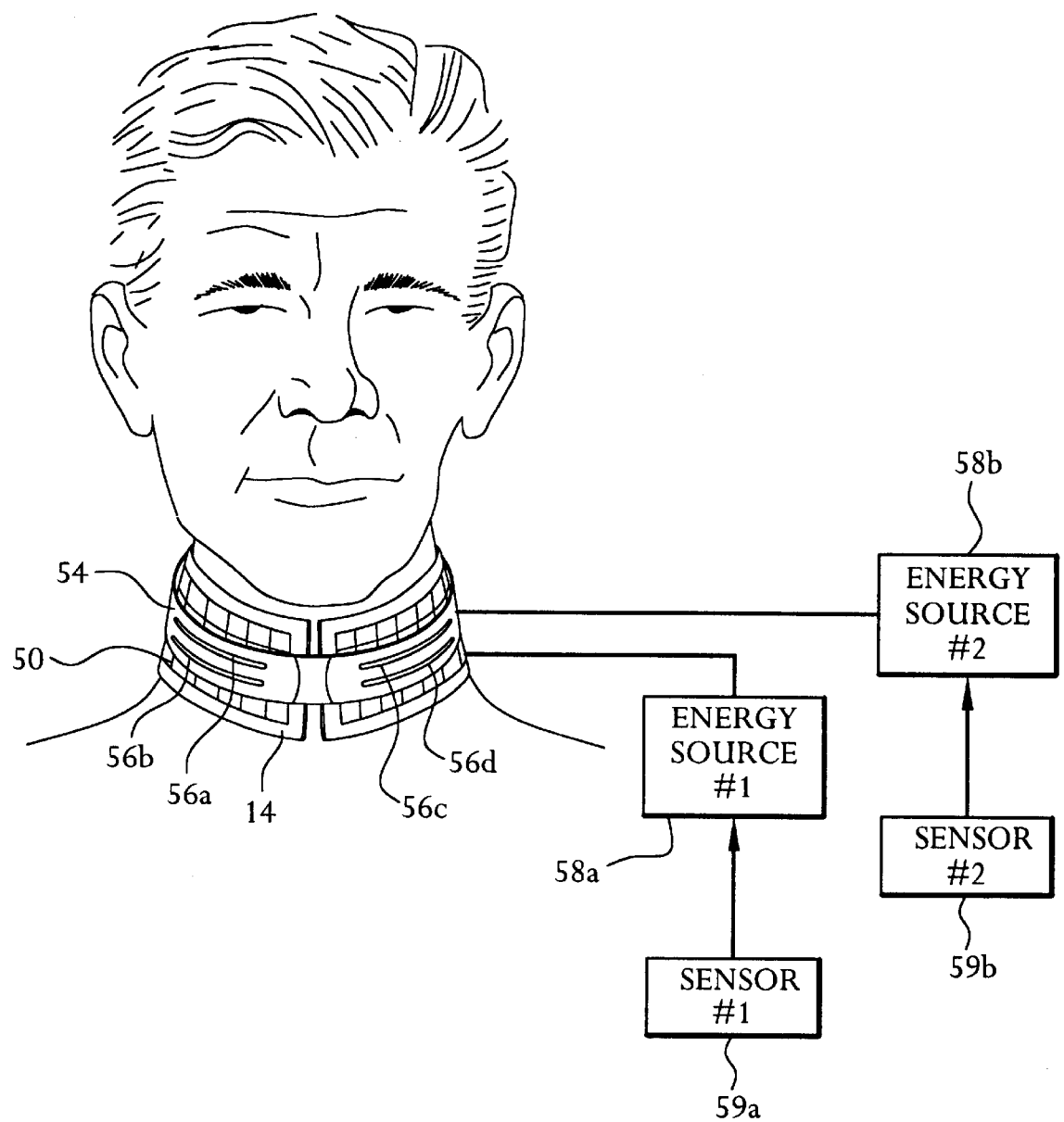
FIG. 6 is an illustration of an embodiment of a composite form of the apparatus according to the invention herein adapted to be externally-disposed on a patient, using an adhesive sheet and a collar.

In yet another embodiment of the externally-applied shape-memory structure, seen in FIG. 6, the two previously mentioned externally-applied embodiments can be combined. A shape-memory structure 50, embedded in an adhesive sheet 14, can be used with a collar 54 which has additional shape-memory structures 56a–d attached thereto. In this embodiment, the respective shape-memory structures 50, 56a–d can receive activation energy from different energy source, 58a, b and can respond to different stimuli from different sensors 59a, b.

The predetermined stimulus as sensed, for example, by sensors 11 and 59a, b in FIGS. 2–6, can be a mechanical, acoustic, optical, electrical, or electromagnetic stimulus, or a combination thereof. Such type of stimulus can be, for example, an electrical or electromagnetic signal from an electroencephalogram, an electrocardiogram, or a transdermal blood gas analyzer, such as a fingertip pulse oximetry device. A suitable transdermal blood gas analyzer, for example, are the BCI9100 Multigas Monitor, by BCI International, Waukesha, WI, and the Onyx Finger Pulse Oximeter by Nonin Medical, Inc., Plymouth, Minn.

With a blood gas sensor, the structures 10, 20, 30, 40, 50, and 56a–d, can be activated when the patient develops a predetermined level of hypoxia, or hypercapnia, during sleep. Another stimulus sensed by sensors 11 and 59a,b could be the sound of the patient's snoring in which acoustical or mechanical vibrations are sensed, causing the energy source, 15, 58a,b, to impart activation energy to structures 10, 20, 30, 40, 50, and 56a–b. It is generally preferred that activation and deactivation of the preconfigured shape-memory structure by sensors 11 and 59a,b to be performed gradually. Controlled structure movement is desirable to the extent that movement of the preconfigured shape-memory structure does not produce arousal in a sleeping wearer, or otherwise be substantially obtrusive to the patient. Also, it is preferred that structure activation and deactivation be responsive to, and perhaps be synchronized with, bodily functions including reflexive functions, for example, the upper pharyngeal reflexive functions of swallowing and coughing.

Figure 7:
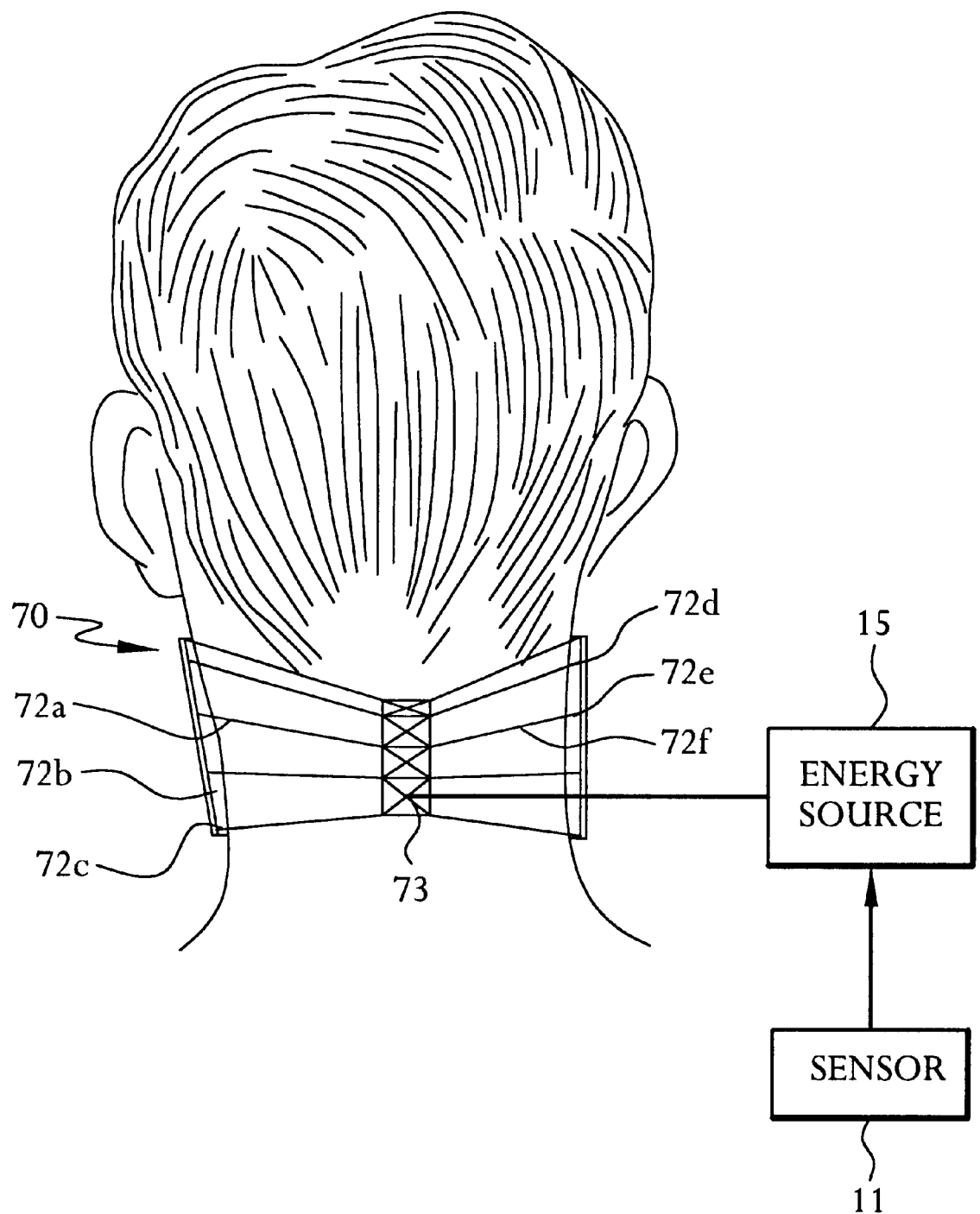
FIG. 7 is an illustration of posterior view of an apparatus as shown in FIGS. 2–6, indicating energy distribution and control connections.

FIG. 7 illustrates one embodiment of energy distribution to shape-memory structure 70. Shape-memory structure electrical leads 72a–f can be posteriorly joined by distribution bus 73 which can be supplied by energy source 15 and activated by sensor ii. Sensor 11 and energy source 15 can be adapted to unobtrusively fit on device 70, thus creating a wearable, self-contained prosthesis.

As previously noted, the preconfigured structure can be implanted in the selected portion of the body. Implantation can be accomplished via a direct surgical incision or percutaneous implantation using a needle approach. In one embodiment of the implanted preconfigured structure, seen in FIG. 8, a linear shape-memory form 80a,b can be implanted into tissue, e.g., one or more suture-like threads of shapememory material can be inserted into the musculature 82a,b,c which form a portion of the pharyngeal wall 83. Muscles 82a,b,c are the superior, middle, and inferior constrictor muscles, respectively, as viewed from the posterior.

For example, linear forms 80a,b can be implanted into the lateral pharyngeal muscles 82a,b,c that form the pharyngeal walls 83. Energy source 85 can be connected to shape-memory forms 80a, b to provide a desired activation energy, responsive to a preselected stimulus for sensor 84. Energy source 85 also may be electrically connected to musculature 82a,b,c so that at least a portion of the activation energy can be used to electrostimulate the attached tissues and induce the contraction of musculature 82a,b,c. This contraction via electrostimulation can augment the force and action produced by applying the activation energy to shape-memory forms 80a,b.

Although sensor 84 and energy source 85 may be externally located, sensor 84 and energy source 85 also may be implanted within the patient's body, if such is desired. When the preconfigured shape-memory structure 80a,b is activated, the activated shape urges the walls 83 of the pharynx outward, thus tending to open the upper airway and overcome the symptoms of obstructive sleep apnea.

Figure 8:
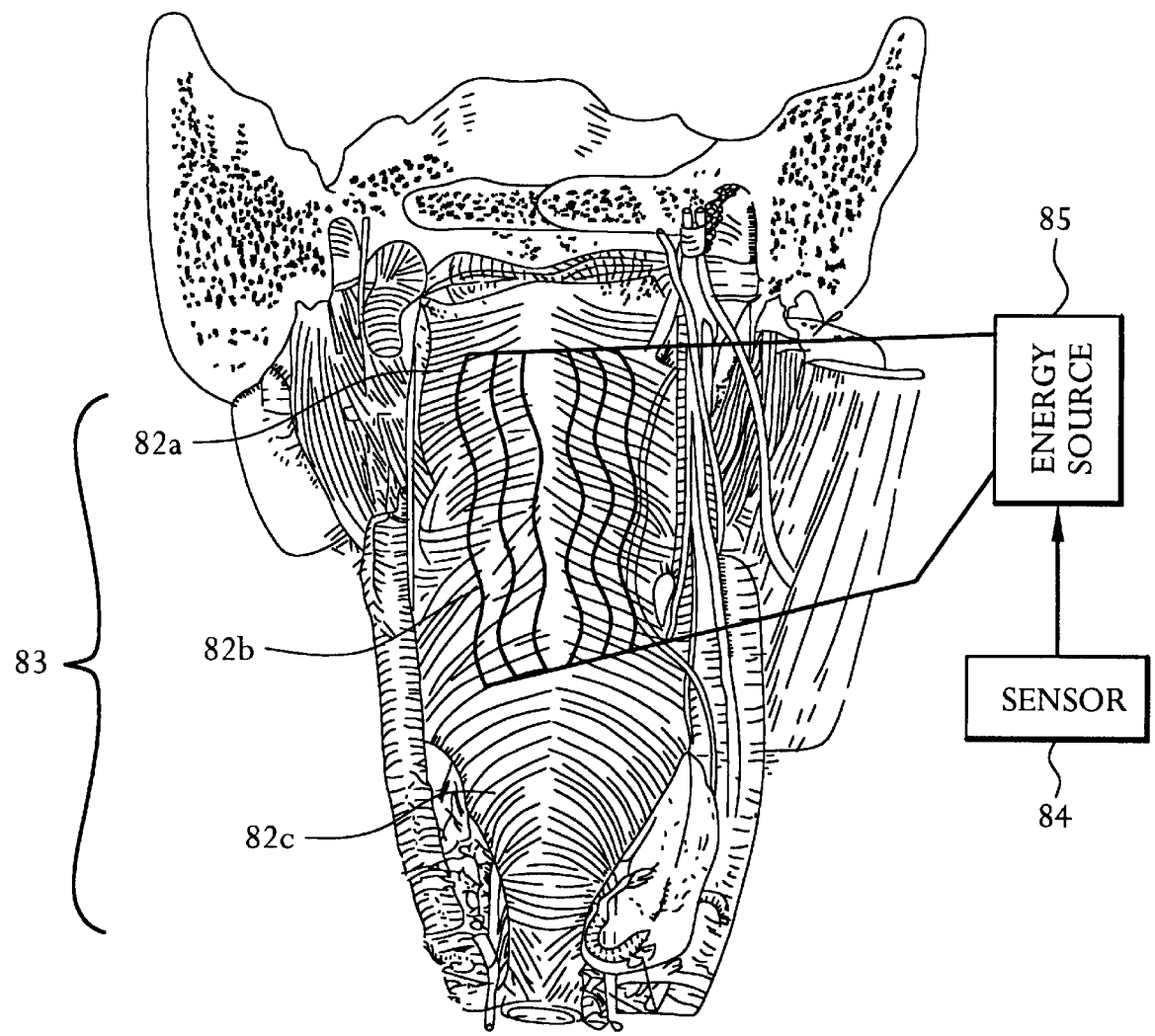
FIG. 8 is an illustration of one embodiment of a linear form of the apparatus according to the invention herein adapted to be implanted within a patient.
Figure 9:
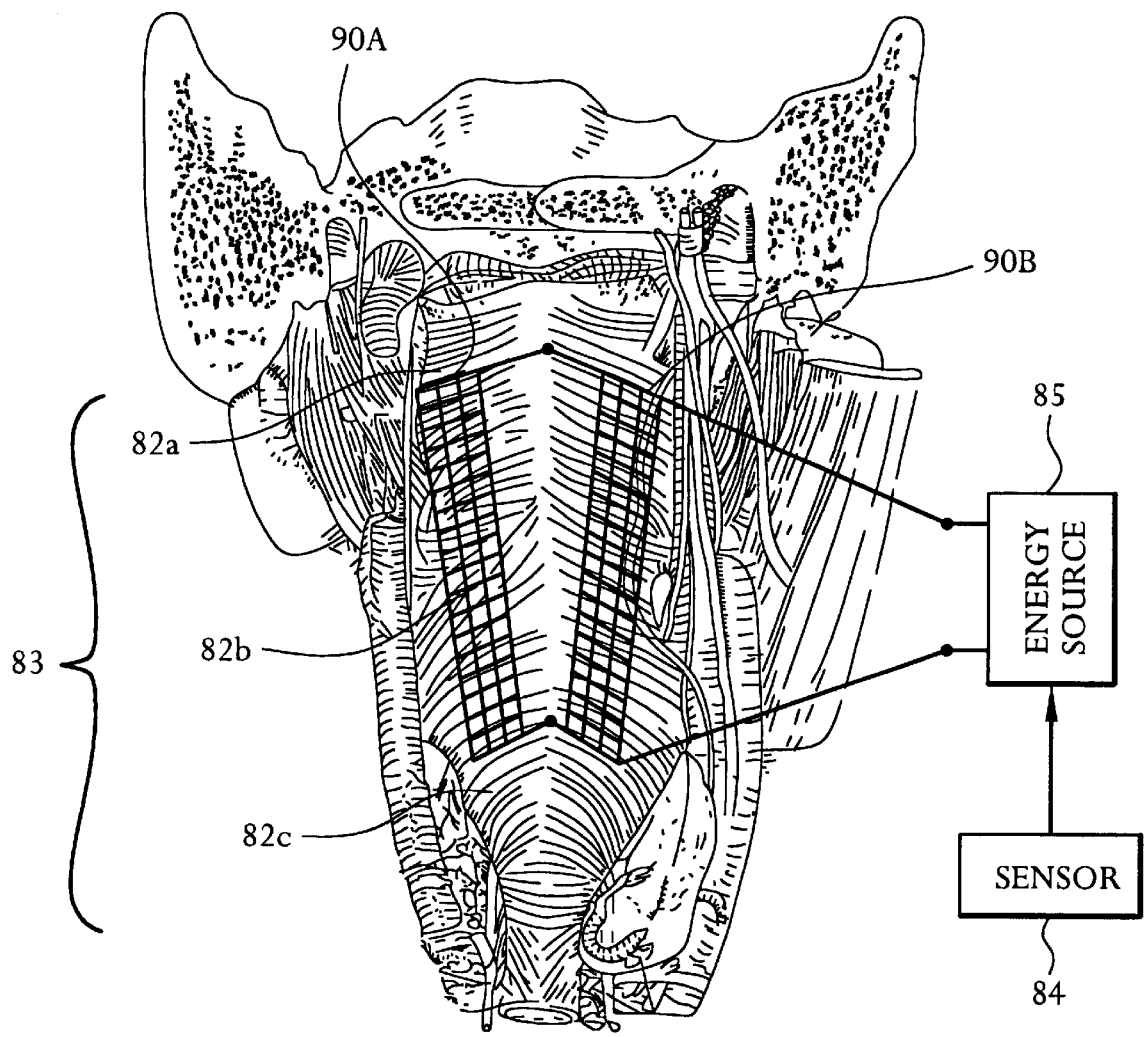
FIG. 9 is an illustration of one embodiment of a planar form of the apparatus according to the invention herein adapted to be implanted within a patient.

Similarly, a planar shape-memory 90a,b form seen in FIG. 9, can be implanted in the muscles 82a,b,c forming the pharyngeal walls 83. Muscles 82a,b,c are the superior, middle, and inferior constrictor muscles, respectively, as viewed from the posterior. Such a planar form 90a,b can be, for example, a mesh or a plate. Similar to the linear form 80 a,b in FIG. 8, the activated shape assumed by the planar form 90a,b, upon activation of the shape-memory material, urges the pharyngeal walls 83 outward, thus tending to open the upper airway and overcome the obstruction causing the sleep apnea. Similar to structure 80a,b in FIG. 8, activation energy can be provided to planar form 90a,b by energy source 85, responsive to a preselected stimulus detected by sensor 84. As in FIG. 8, energy source 85 also may be electrically connected to musculature 82a,b,c so that at least a portion of the activation energy can be used to stimulate the attached tissues and induce the contraction of musculature 82a,b,c. This contraction via electrostimulation can augment the force and action produced by applying the activation energy to planar form 90a,b.

Furthermore, sensor 84 and energy source 85 can be located externally, to or implanted within, the body of the patient.

Figure 10:
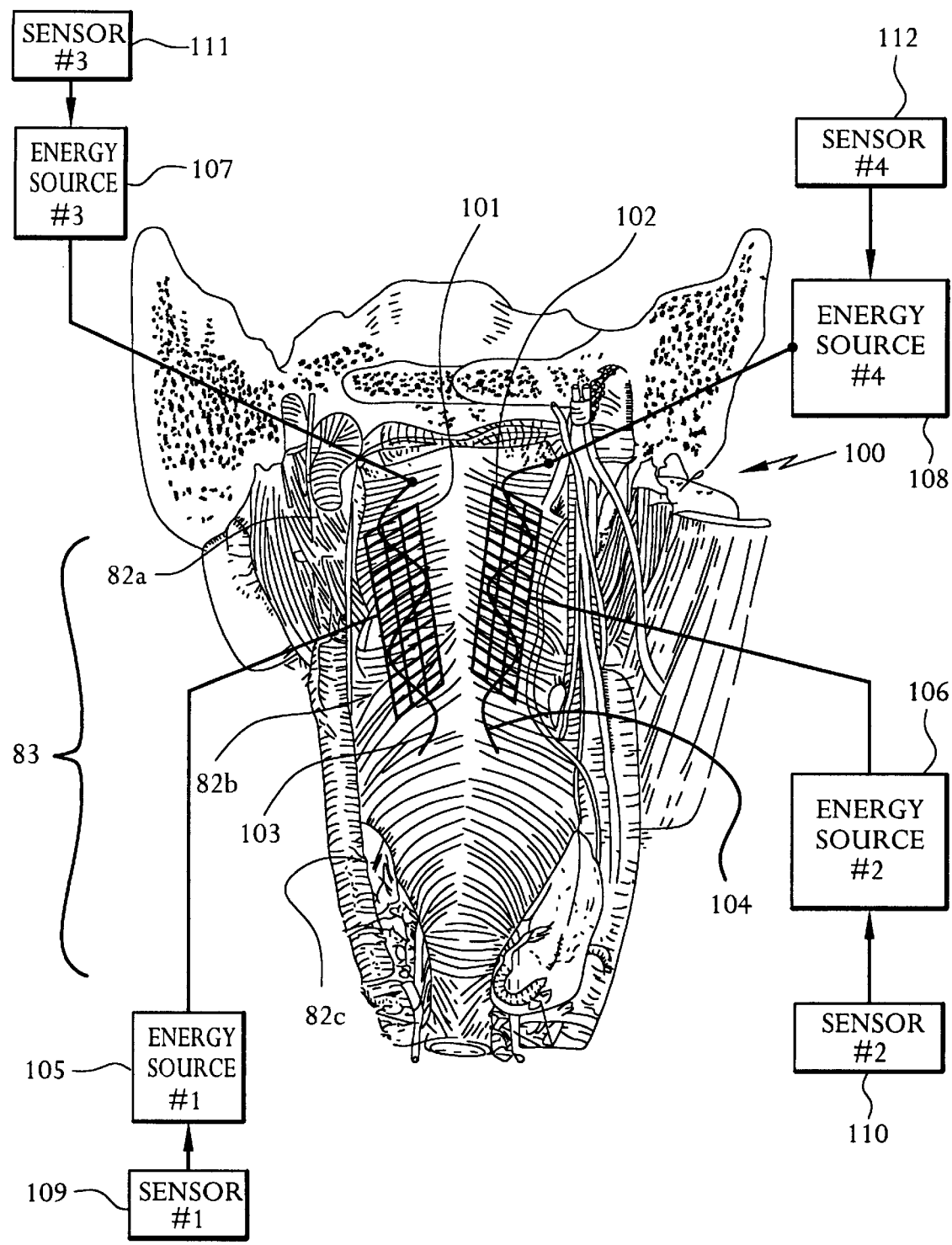
FIG. 10 is an illustration of one embodiment of a composite form of the apparatus according to the invention herein adapted to be implanted within a patient.
Figure 11:
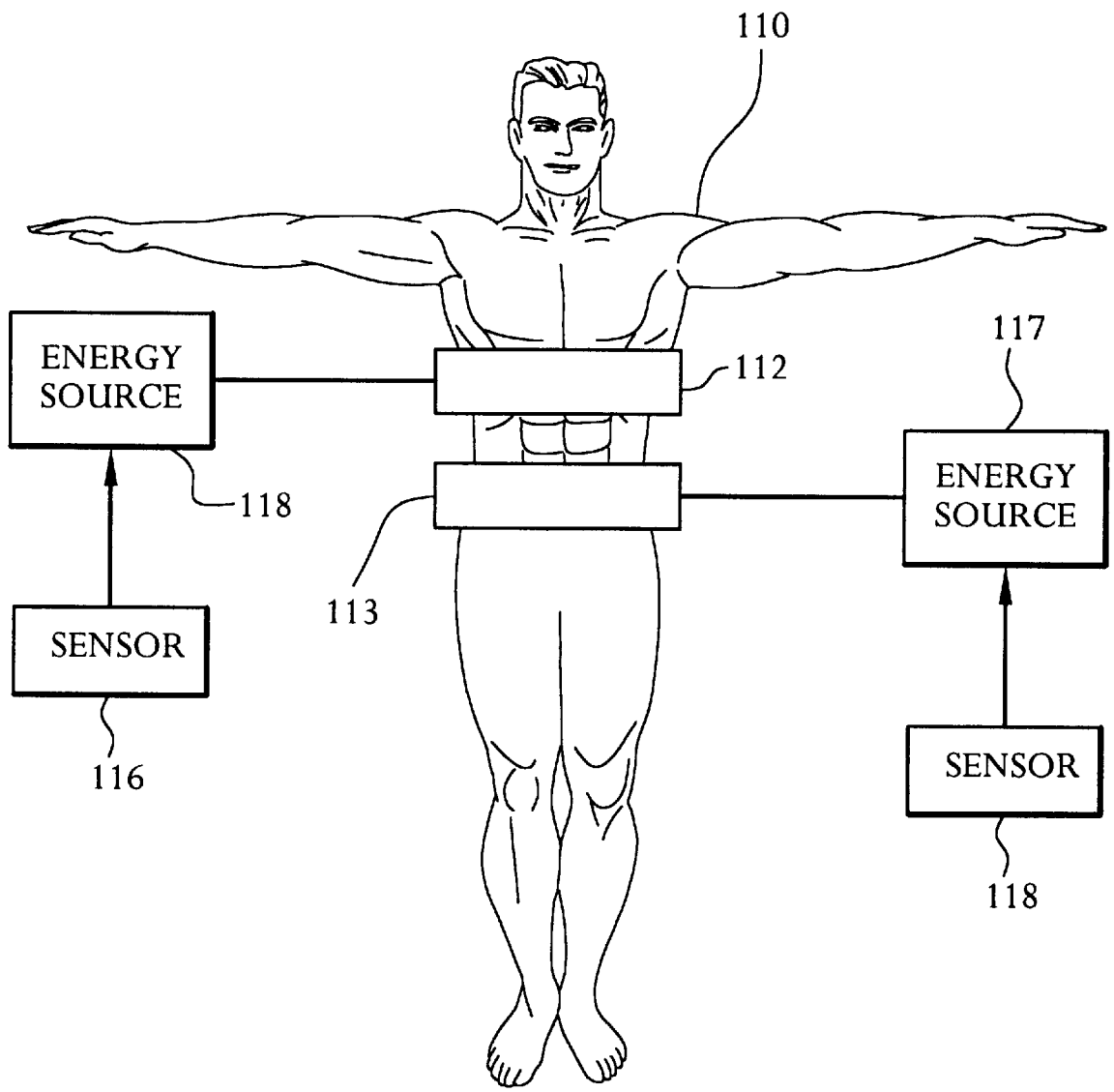
FIG. 11 is an illustration of embodiments of the apparatus according to the invention herein adapted to fit around the torso of a patient.

Also, in some embodiments of the apparatus according to the invention herein, it may be desired to construct a composite preconfigured shape-memory structure 100 from a plurality of planar forms 101, 102, linear forms 103, 104, or both, as seen in FIG. 10. By selectively activating specific ones of the shape-memory forms 101–104, multiple activated shapes can be obtained from composite structure 100. In this way, the outward force upon pharynx 114 can be varied as desired by the physician. For the purpose of illustration, structure 100 in FIG. 10 includes four separate shape-memory forms, namely, planar forms 101 and 102, and linear forms 103 and 104. If desired, each of forms 103 and 104 independently can receive activation energy from respective energy source, 105–108, responsive to predetermined stimuli as sensed by respective sensors 109–112. Energy source, 105–108 and sensors 109–112 can be externally located, or can be implanted within the patient.

As in FIGS. 8 and 9, muscles 82a,b,c in FIG. 10 are the superior, middle, and inferior constrictor muscles, respectively, as viewed from the posterior. One or more of energy source, 105–108 also may be electrically connected to musculature 82a,b,c so that at least a portion of the activation energy can be used to stimulate the attached tissues and induce the contraction of musculature 82a,b,c. As in the linear form of FIG. 8, and the planar form of FIG. 9, this contraction via electrostimulation can augment the force and action produced by applying the activation energy to composite structure 100. One skilled in the art will appreciate that multiple design permutations are possible, as are specific placement sites for the shape-memory structures.

Although the apparatus and method herein have been described in terms of embodiments suitable for the treatment of sleep apnea, it must be understood that the apparatus and method herein also may be used for other conditions and clinical states in which it is desired to reversibly modify the shape of the selected portion of the body. For example, where it is desired to augment the respiratory function of patient 110, a shape memory structure can be configured as a chest harness or band 112, or as an abdominal girdle or belt 113, depending upon the nature of the assistance desired. Both band 112 and belt 113 are shown, however, only one of which may be used. Band 112 and belt 113 can be designed to apply a compressive force to patient 110 to augment end-expiratory gas movement out of the lungs. This approach may be useful for patients with obstructive lung disease. Band 112 and belt 113 also can be designed to provide an outward, expansive force to assist patient 110 during inspiration. Additionally, band 112 and belt 113 can be designed to provide both compression and expansion forces which may be coordinated with, and adapted to augment, the patient's normal respiratory cycle. Band 112 can receive activation energy from energy source 115, responsive to sensor 116. Similarly, belt 113 can receive activation energy from energy source 117, responsive to sensor 118.

While specific embodiments of practicing the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting to the scope of the invention which is to be given the full breadth of the following claims, and any and all embodiments thereof.

I claim:

1. An apparatus for reversibly modifying the shape of a selected portion of a body, comprising:
   a. a preconfigured structure having a shape-memory, the preconfigured structure having an activated shape and a quiescent shape;
   b. the preconfigured structure being shaped to conform to the selected portion of the body, the preconfigured structure being connectable to the selected portion, the shape-memory being responsive to an activation energy and urging the preconfigured structure from the quiescent shape to the activated shape;
   c. the activated shape of the preconfigured structure adapted to exert a force on the selected portion, thereby tending to modify the shape of the selected portion; and
   d. wherein the shape memory responds to removal of the activation energy by urging the preconfigured structure from the activated shape to the quiescent shape and at least partially removing the force on the selected portion of the body thus tending to restore the shape of the selected portion of the body.

2. The apparatus of claim 1 wherein the preconfigured structure is adapted to be attached to an exterior surface of the selected portion of the body.

3. The apparatus of claim 2 wherein the activation energy is applied gradatim.

4. The apparatus of claim 2 wherein the activation energy is intermittently applied.

5. The apparatus of claim 1 wherein the preconfigured structure is adapted to be implanted within the body proximate to the selected portion.

6. The apparatus of claim 1 further comprising an energy source for providing the activation energy, the energy source being coupled with the preconfigured structure, the energy source being responsive to a predetermined stimulus.

7. The apparatus of claim 6 wherein the energy source is selected from the group consisting of an electrical energy source, a mechanical energy source, a thermal energy source and an electromagnetic energy source.

8. The apparatus of claim 7, wherein the predetermined stimulus is selected from the group consisting of a mechanical stimulus an electrical stimulus, an electromagnetic stimulus, an acoustic stimulus and an optical stimulus.

9. The apparatus of claim 8, wherein the energy source is external to the surface of the body.

10. The apparatus of claim 9, wherein the activation energy is applied gradatim so that the modifying and restoring of the shape of the selected portion is substantially unobtrusive.

11. The apparatus of claim 9, wherein the activation energy is intermittently applied to accommodate a function of the body.

12. The apparatus of claim 8, wherein the energy source is adapted to be implanted within the body.

13. The apparatus of claim 8, wherein exerting the force is performed gradatim so that modifying the shape of the selected portion is substantially unobtrusive.

14. The apparatus of claim 8, wherein the shape-memory responds to removal of the activation energy, and urges the preconfigured structure from the activated shape to the quiescent shape, thereby at least partially removing the force on the selected portion, thereby tending to restore the shape of the selected portion.

15. The apparatus of claim 6, wherein the activation energy is applied gradatim so that the modifying and restoring of the shape of the selected portion is substantially unobtrusive.

16. The apparatus of claim 1 wherein the force is exerted gradatim.

17. The apparatus of claim 16, wherein the activation energy is applied gradatim.

18. The apparatus of claim 1 wherein the preconfigured structure is selected from the group consisting of a first linear form and a first planar form.

19. The apparatus of claim 18, wherein the planar form includes a plurality selected from the group consisting of a second linear form, a second planar form, ones of each plurality of forms being selectively activatable.

20. The apparatus of claim 1 wherein the selected portion of the body is a pharyngeal wall and the activated shape of the structure is adapted to exert onward force on the wall, thereby tending to urge open the pharynx.

21. The apparatus of claim 20, further comprising an energy source for providing the activation energy, the energy source being coupled with the preconfigured structure and being responsive to a predetermined stimulus.

22. The apparatus of claim 21, wherein the energy source is selected from the group consisting of an electrical energy source, a mechanical energy source, a thermal energy source and an electromagnetic energy source.

23. The apparatus of claim 22, wherein the predetermined stimulus is selected from the group consisting of a mechanical stimulus, electromagnetic stimulus, electrical stimulus, acoustic stimulus and optical stimulus.

24. The apparatus of claim 23, wherein the energy source is external to the surface of the body.

25. The apparatus of claim 23, wherein the energy source is adapted to be implanted within the body.

26. The apparatus of claim 23, wherein:
   a. the preconfigured structure is selected from the group consisting of a linear form, a planar form, and a composite form, and the preconfigured structure is adapted to be affixed to the tissues proximate to the pharyngeal wall;
b. the linear form is selected from the group consisting of a single-stranded thread, a multistranded braid, and a strip;
c. the planar form is selected from the group consisting of a mesh and a plate;
d. the composite form is a plurality selected from the group consisting of one of the linear form and the planar form;
e. the shape-memory responds to removal of the activation energy, and urges the preconfigured structure from the activated shape to the quiescent shape, thereby tending to restore the shape of the pharyngeal wall; and
f. the activation energy is selectively applied so that the modifying and restoring is substantially unobtrusive.

27. The apparatus of claim 26, wherein the activation energy applied with is selected from the group consisting of intermittently, gradatim and synchronously with a body function so that the modifying and restoring is substantially unobtrusive and the body function is accommodated.

28. The apparatus of claim 20, wherein the preconfigured structure is adapted to be attached to an exterior surface of the neck proximate to the pharyngeal wall.

29. The apparatus of claim 28, wherein the preconfigured structure is selected from the group consisting of a linear form and a planar form.

30. The apparatus of claim 29, further comprising an adhesive form adaptable to be at least partially interposed between the preconfigured structure and the exterior surface of the neck, the adhesive form adapted for removably attaching the preconfigured structure to the exterior surface of the neck.

31. The apparatus of claim 29, further comprising a collar and at least one adhesive pad, the collar having the preconfigured structure therein, the at least one adhesive pad adapted for removably attaching the preconfigured structure to the exterior surface of the neck.

32. The apparatus of claim 29, further comprising an energy source for providing the activation energy, the energy source being coupled with the preconfigured structure and being responsive to a predetermined stimulus.

33. The apparatus of claim 32, wherein:
a. the energy source is selected from the group consisting of an electrical energy source, a mechanical energy source, a thermal energy source and an electromagnetic energy source; and
b. the predetermined stimulus is selected from the group consisting of a mechanical stimulus, an electrical stimulus, an electromagnetic stimulus, an acoustical stimulus and an optical stimulus.

34. The apparatus of claim 33, wherein:
a. the preconfigured structure is selected from the group consisting of a linear form, a planar form, and a composite form, and the preconfigured structure is adapted to be affixed to the tissues proximate to the pharyngeal wall;
b. the linear form is selected from the group consisting of a single-stranded thread, a multistranded braid, and a strip;
c. the planar form is selected from the group consisting of a mesh and a plate;
d. the composite form is a plurality of at least one selected from the group consisting of linear form and the planar form;
e. the shape-memory responds to removal of the activation energy, and urges the preconfigured structure from the activated shape to the quiescent shape, thereby tending to restore the shape of the pharyngeal wall; and
f. the activation energy is selectively applied so that the modifying and restoring is substantially unobtrusive.

35. The apparatus of claim 34, wherein the activation energy applied is selected from the group consisting of intermittently, gradatim and synchronously with a body function so that the modifying and restoring is substantially unobtrusive and the body function is accommodated.

36. The apparatus of claim 20, wherein the preconfigured structure is adapted to be implanted within a tissue proximate to the pharyngeal wall.

37. The apparatus of claim 36, wherein the preconfigured structure is selected from the group consisting of a linear form and a planar form.

38. The apparatus of claim 37, further comprising an energy source for providing the activation energy, the energy source being coupled with the preconfigured structure and being responsive to a predetermined stimulus.

39. The apparatus of claim 38, wherein:
a. the energy source is selected from the group consisting of an electrical energy source, a mechanical energy source, a thermal energy source and an electromagnetic energy source; and
b. the predetermined stimulus is selected from the group consisting of a mechanical stimulus, an electrical stimulus, an electromagnetic stimulus, an acoustical stimulus and an optical stimulus.

40. The apparatus of claim 37, wherein:
a. the preconfigured structure is the linear form, which linear form is selected from the group consisting of a single-stranded thread, a multi-stranded braid, and a strip; and
b. the linear form is adapted to be affixed to tissues proximate to the pharyngeal wall.

41. The apparatus of claim 37 wherein:
a. the preconfigured structure is the planar form, which planar form is selected from the group consisting of a mesh and a plate; and
b. the planar form is adapted to be affixed to tissues proximate to the pharyngeal wall.

42. The apparatus of claim 20, wherein the preconfigured structure is selected from the group consisting of a first linear form and a first planar form.

43. The apparatus of claim 42, wherein the planar form includes a plurality selected from the group consisting of a second linear form, a second planar form, ones of the plurality of forms being selectively activatable.

44. the apparatus of claim 1 wherein the selected portion of the body is selected from the group consisting of the chest and the abdomen, and the activated shape of the structure exerts a force upon the selected portion, thereby tending to assist respiratory function.

45. The apparatus of claim 44, further comprising an energy source for providing the activation energy, the energy source being coupled with the preconfigured shape-memory structure and being responsive to a predetermined stimulus.

46. The apparatus of claim 45, wherein the energy source is selected from the group consisting of a mechanical energy source, a thermal energy source and an electromagnetic energy source.

47. The apparatus of claim 46, wherein the predetermined stimulus is selected from the group consisting of a mechanical stimulus, an electromagnetic stimulus, an electrical stimulus, and acoustic stimulus and an optical stimulus.

48. The apparatus of claim 44, wherein the preconfigured structure is selected from the group consisting of a linear form and a planar form.

49. A method for reversibly modifying the shape of a selected portion of a body comprising the steps of:

a. attaching a preconfigured shape-memory structure to the selected portion, the structure having a shape-memory being shaped to generally conform to the selected portion, the structure having an activated shape and a quiescent shape, the shape-memory being responsive to an activation energy; and b. applying the activation energy to the preconfigured structure, thereby transforming the preconfigured shape-memory structure from the quiescent shape to the activated shape, the activated shape exerting a force upon selected portion, thereby tending to modify the shape of the selected portion.

50. The method of claim 49, wherein applying the activation energy includes the steps of:

a. sensing a predetermined condition;

b. generating a stimulus responsive to the predetermined condition; and c. generating the activation energy responsive to the stimulus.

51. The method of claim 49, wherein the step of attaching includes interposing an adhesive pad between the selected portion and the preconfigured shape-memory structure, the structure being at least partially embedded in the adhesive pad, the adhesive pad being removably attached to an exterior surface of the body proximate to the selected portion, the adhesive pad transmitting the force to the external surface from the activated shape, responsive to the activation energy.

52. The method of claim 51, wherein the shape-memory structure is connected to an energy source and further comprising the steps of:

a. sensing a predetermined condition;

b. generating a stimulus responsive to the predetermined condition; and c. generating the activation energy responsive to the stimulus.

53. The method of claim 50 wherein the step of attaching includes implanting the preconfigured shape-memory structure in the body proximate to the selected portion.

54. The method of claim 53 wherein the shape-memory structure is connected to an energy source, and further comprising the steps of:

a. sensing a predetermined condition;

b. generating a stimulus responsive to the predetermined condition; and c. generating the activation energy responsive to the stimulus.

55. The method of claim 49, wherein the step of attaching includes removably attaching a collar, belt, or band to the selected portion, the collar, belt, or band having the preconfigured shape-memory structure therein.

56. The method of claim 49, wherein the shape-memory structure is connected of an energy source, and further comprising the steps of:

a. sensing a predetermined condition;

b. generating a stimulus responsive to the predetermined condition;

c. selectively generating the activation energy responsive to the stimulus, the selectively generating including those selected from the group consisting of intermittent generating, gradatim generating, and synchronously generating so that the reversibly modifying is substantially unobtrusive is substantially unobtrusive.

* * * * *